(12) United States Patent
Nathan et al.

(10) Patent No.: US 7,984,660 B2
(45) Date of Patent: Jul. 26, 2011

(54) PIPELINE SAMPLING DEVICE

(76) Inventors: Scott Roger Nathan, Canning Vale (AU); Adrian van Dolder, Edmonton, Alberta (CA); Christopher Todd Kozak, Fort Saskatchewan, Alberta (CA)

( * ) Notice: Subject to any disclaimer, the term of this patent is extended or adjusted under 35 U.S.C. 154(b) by 677 days.

(21) Appl. No.: 11/658,027

(22) PCT Filed: Jul. 22, 2005

(86) PCT No.: PCT/AU2005/001073
§ 371 (c)(1),
(2), (4) Date: Aug. 24, 2007

(87) PCT Pub. No.: WO2006/007655
PCT Pub. Date: Jan. 26, 2006

(65) Prior Publication Data
US 2008/0098829 A1    May 1, 2008

(30) Foreign Application Priority Data
Jul. 23, 2004    (AU) ................................. 2004904055

(51) Int. Cl.
*G01N 1/14* (2006.01)
(52) U.S. Cl. .................................................. 73/863.83
(58) Field of Classification Search ............... 73/863.82, 73/863.83, 863.85, 863.86, 864.34
See application file for complete search history.

(56) References Cited

U.S. PATENT DOCUMENTS

| | | | | |
|---|---|---|---|---|
| 3,007,340 A * | 11/1961 | Kraftson | ....................... | 73/866.5 |
| 4,562,749 A | 1/1986 | Clark | | |
| 4,628,732 A * | 12/1986 | Makinen | ....................... | 73/866.5 |
| 4,771,642 A * | 9/1988 | Parth et al. | ................. | 73/863.52 |
| 5,234,205 A * | 8/1993 | Shanley | .......................... | 269/99 |
| 5,406,855 A | 4/1995 | Welker | | |
| 6,164,145 A * | 12/2000 | Jaeger | ......................... | 73/863.83 |
| 6,357,306 B1 * | 3/2002 | Jaeger | ......................... | 73/863.83 |
| 6,792,818 B2 * | 9/2004 | Jaeger | ......................... | 73/863.86 |
| 2002/0166392 A1 * | 11/2002 | Handel | ....................... | 73/863.83 |
| 2003/0159524 A1 * | 8/2003 | Jaeger | ......................... | 73/863.83 |

FOREIGN PATENT DOCUMENTS

| | | |
|---|---|---|
| DE | 2 932 992 A | 4/1981 |
| DE | 4 316 734 A | 12/1993 |
| SU | 5 833 82 A | 12/1977 |

* cited by examiner

*Primary Examiner* — Robert R Raevis
(74) *Attorney, Agent, or Firm* — Walker & Jocke; Brett A. Schenck; Ralph E. Jocke

(57) ABSTRACT

A sampling device (10) includes a sample extraction portion (28) which reciprocates within a cylindrical sample housing portion (26). The sample housing portion is axially moveable through a gate valve (22) to permit removal and maintenance of the sample extractor.

19 Claims, 2 Drawing Sheets

PIPELINE SAMPLING DEVICE

FIELD OF THE INVENTION

The present invention relates to a sampling device such as one for use in process sampling, including the sampling of fluids, slurries, and powders

BACKGROUND TO THE INVENTION

It is known to require the extraction of sample quanta from pipelines and other process flow operations. Such sampling is required in many types of operations, including oil and gas processing, mineral processing, chemical processing, food preparation and pharmaceutical preparation.

A known type of sampling device is bolted to the side of a pipeline, and comprises a rod which slides through a cylindrical tube aligned radially to the pipeline. The rod includes two sets of axially separated circumferential seals which engage with inner walls of the tube, and a sample spool piece located between the two sets of seals. In order to acquire a sample, an end of the rod including an outer circumferential seal set and the sample spool piece are moved axially from the tube into the pipeline. Product from within the pipeline thus flows about the sample spool piece, up to the second, inner circumferential seal set. The rod is then withdrawn into the tube, with a sample being held in the sample spool piece between the two seals. The rod is withdrawn a sufficient distance that the inner seal passes over an aperture, through which the sample is extracted for testing.

There are several drawbacks to use of such a device. Principal amongst these is that the outer circumferential seal set slides within the tube, and is thus subject to wear. During normal product flow within the pipeline, when sampling is not occurring, this outer seal set is required to prevent leakage from the pipeline. As such, should wear occur, the pipeline must be shut down and emptied in order for the seal set to be replaced.

The present invention attempts to overcome at least in part some of the aforementioned disadvantages of previous sampling devices.

SUMMARY OF THE INVENTION

In accordance with one aspect of the present invention there is provided a sampling device for extracting a sample from a pipe, the sampling device comprising a sample housing portion and a sample extracting portion, the sample extracting portion being moveable relative to the sample housing portion, characterised in that the sample housing portion is movable relative to the pipe. Advantageously, this permits separate seals to be employed between the sample extracting portion and the sample housing portion, and the sample housing portion and the pipe.

Preferably, the sample housing portion is operatively associated with a primary valve means, such that the sample housing portion may be fluidly connected to the pipe when the primary valve means is in an open configuration, and the primary valve means seals the pipe against the sample housing portion when the primary valve means is in a closed configuration. This permits the sample housing portion to be removed for maintenance or other reasons whilst maintaining the integrity of the pipe.

BRIEF DESCRIPTION OF THE DRAWINGS

The present invention will now be described, by way of example, with reference to the accompanying drawings, in which.

DESCRIPTION OF PREFERRED EMBODIMENTS

Figure 1:
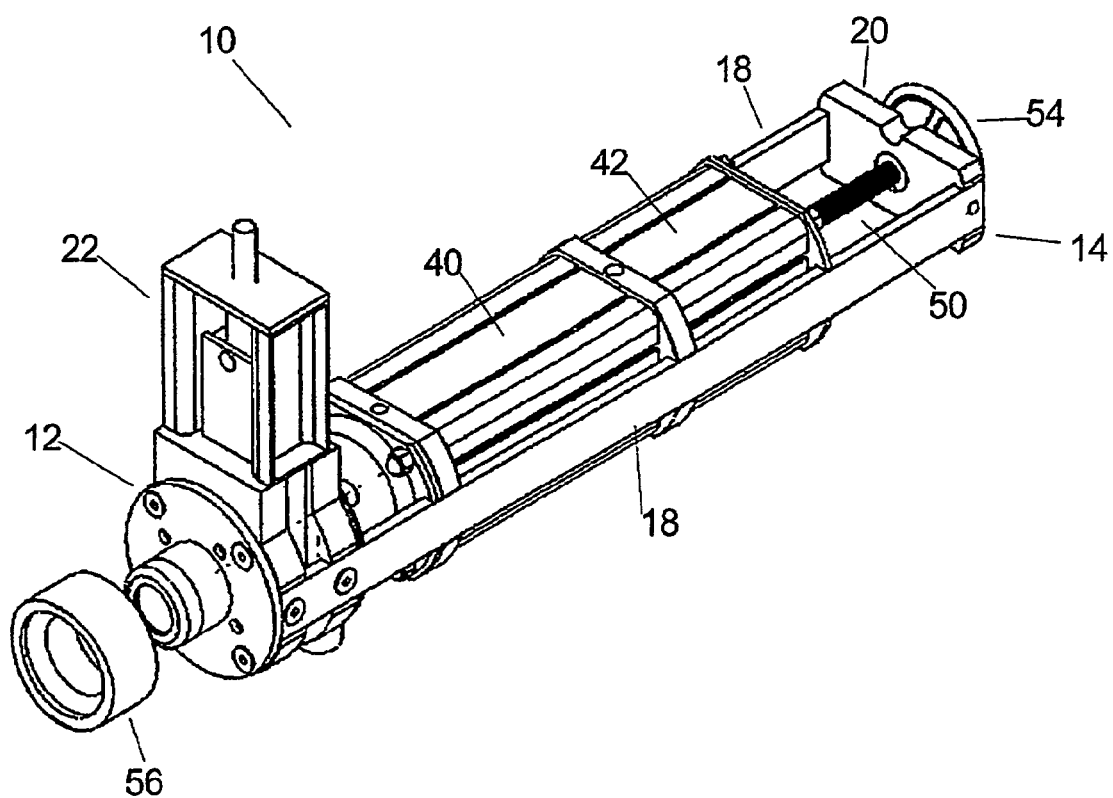
FIG. 1 is an isometric view of a sampling device in accordance with the present invention.

Referring to the Figures, there is shown a sampling device 10.

The sampling device 10 extends from a first or inner end 12 adjacent, in use, a pipe (not shown) to a second or outer end 14 remote from the pipe. The first end 12 includes a connecting flange 16 which may be connected to the pipe. A pair of side rails 18 extend from the connecting flange 16 to the second end 14. At the second end 14 the side rails are connected to an endplate 20.

The sampling device 10 includes a primary valve means located adjacent the first end 12. In a preferred embodiment, as shown in the drawings, the primary valve means is a knife gate valve 22. The knife gate valve 22 is bolted to the side rails 18.

The knife gate valve 22 has a central bore 24. The central bore extends through the knife gate valve 22, and the connecting flange 16 and into the pipe, and is substantially cylindrical.

Figure 2:
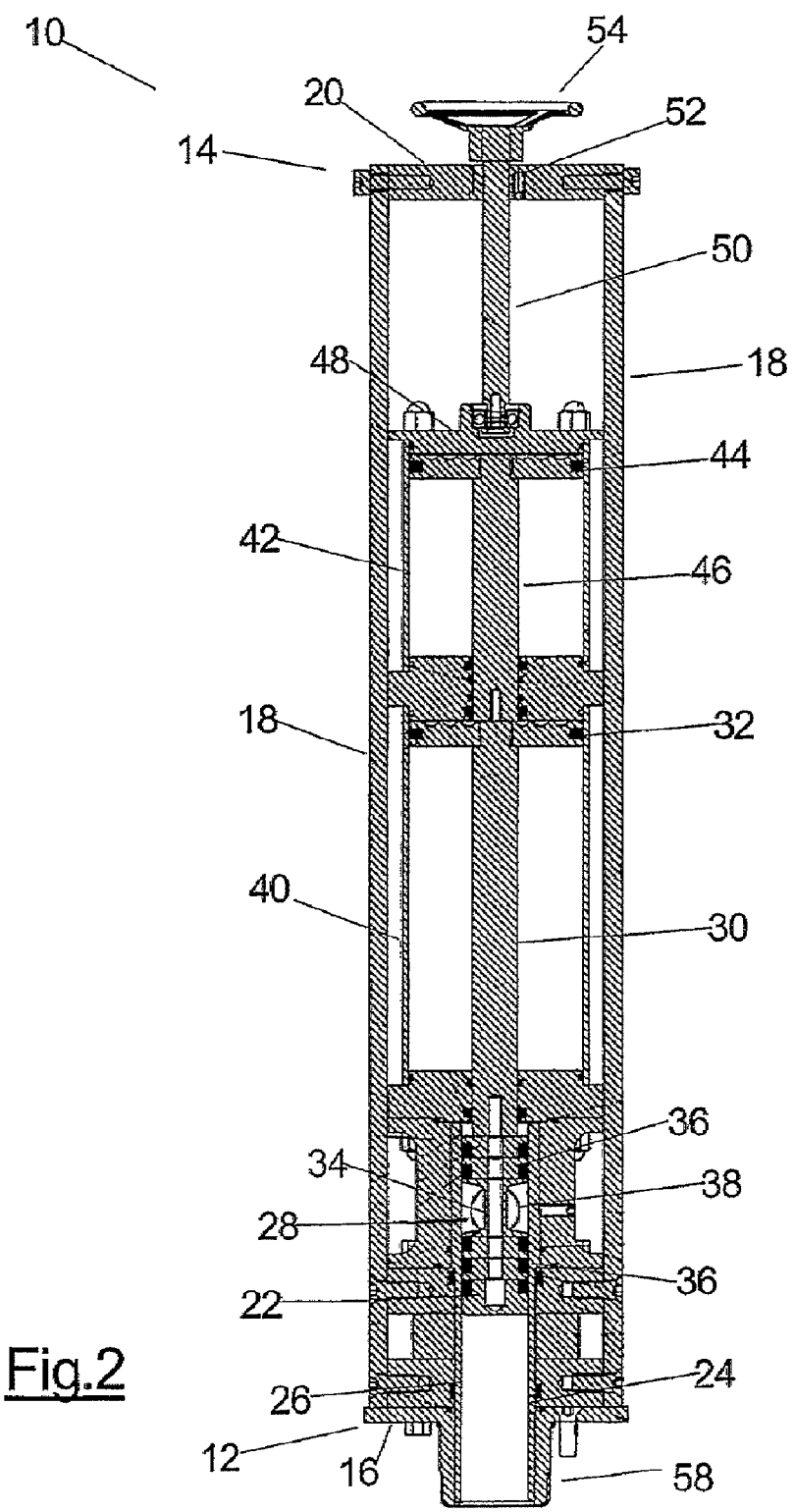
FIG. 2 is a cross sectional view of the sampling device of FIG. 1.
Figure 2:
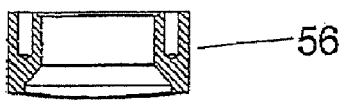

The sampling device 10 further comprises a sample housing portion 26. The sample housing portion 26 is substantially cylindrical, with an external diameter sized to be in sliding, sealed relationship with the central bore 24. The sample housing portion 26 is moveable relative to the pipe, between an active position wherein the sample housing portion 26 extends through the knife gate valve 22 (as shown in FIG. 2) and the connecting flange 16 and an inactive position wherein the sample housing portion 26 locates outside the knife gate valve 22. The sample housing portion 26 is fluidly connected to the pipe when in the active position.

A sample extracting means is actively associated with, and moveable relative to, the sample housing portion 26. The sample extracting means comprises a sample extracting portion 28, a first activating rod 30 and a first piston 32.

The sample extracting portion 28 includes a spool 34 fixed between disc-like seals 36. The disc-like seals 36 are in sliding, sealing engagement with an internal bore of the sample housing portion 26. An annular space 38 of defined volume is located between the spool 34 and the internal bore of the sample housing portion 26.

The first activating rod 30 is coaxial with, and of slightly smaller diameter than, the disc-like seals 36. The first activating rod 30 is mounted at an inner end thereof to a rearmost of the disc-like seals 36. Axial movement of the first activating rod 30 thus causes the sample extracting portion 28 to slide along and within the sample housing portion 26.

The first piston 32 is mounted to an outer end of the first activating rod 30. The first piston 32 is in sliding engagement with the interior of a first cylinder 40. The first cylinder 40 is mounted on the side rails 18 so as to be axially movable along the side rails 18. The first cylinder 40 is fixed at an inner end thereof to the sample housing portion 26, such that axial movement of the first cylinder 40 along the side rails 18 causes axial movement of the sample housing portion 26 within the central bore 24. The stroke of the first piston 32 within the first cylinder 40 is sufficiently long that when the first piston 32 is at an outer end of the first cylinder 40 the spool 34 is adjacent an outer end of the sample housing portion 26 (as shown in FIG. 2), and when the first piston 32 is at an inner end of the first cylinder 40 the spool 34 extends beyond the first end 12 of the sampling device 10 into the pipe.

The first cylinder 40 is fixed at an outer end thereof to a second cylinder 42. The second cylinder 42 is mounted to the side rails 18 so as to be axially moveable along the side rails 18 in unison with the first cylinder 40.

The second cylinder 42 has a second piston 44 in sliding engagement with its interior, and a second activating rod 46 associated with the second piston 44. The second activating rod 46 pushes against the first piston 32, such that when the second piston 44 moves towards the first end 12 the first piston 32 is caused to move in unison. The second activating rod 46 is not coupled to the first piston 32, so movement of the second piston 44 towards the second end 14 does not cause movement of the first piston 32.

The stroke of the second piston 44 is smaller than that of the first piston 32. It is sufficiently long to move the sample extracting portion 28 to a location adjacent the first end 12 of the sampling device 10, and the inner end of the sample housing portion 26, but not sufficiently long to move the extracting portion 28 into the pipe. The second cylinder 42 is sealed at an outer end thereof by a cylinder end cap 48.

A threaded rod 50 extends between the end plate 20 and the cylinder end cap 48. The threaded rod 50 is connected centrally of the cylinder end cap 48 in such a manner that it can rotate freely whilst remaining connected. The threaded rod 50 passes through a centrally located, threaded aperture 52 in the end plate 20 and is fixed to a handle 54.

Rotation of the handle 54 causes the rod to move in an axial direction though the aperture 52. In turn, this causes the second cylinder 42, the first cylinder 40 and the sample housing portion 26 to move along the side rails 18 in an axial direction.

The knife gate valve 22 is preferably a double knife gate valve, with bleed points located behind each of the knives.

The first and second pistons 32,44 are preferably pneumatically controlled, with air supply points within the first and second cylinders 40, 42 at either end.

In the embodiment shown in the drawings, the sampling device 10 is associated with a weld-on adaptor 56. The weld-on adaptor 56 is arranged to be welded onto the wall of the pipe, and provide a housing against which the connection flange 16 can be bolted. In this embodiment the sampling device includes a forwardly projecting portion 58 which is arranged to locate within the weld-on adaptor 56.

In use, the knife gate valve 22 is moveable between an open configuration and a closed configuration. In the open configuration, the sample housing portion 26 is able to move in an axial direction within the central bore 24 into the active position.

When the sample housing portion 26 is in the active position, sampling can take place.

When the sample housing portion 26 is in the active position, the sample extending portion 28 can move between three positions: a collecting position, a neutral position and an emptying position.

In the collecting position, the spool 34 is located beyond the first end 12 of the sampling device 10, in other words the spool 34 is within the pipe. As the spool 34 is withdrawn into the sample housing portion 26, the annular space 38 is filled with a defined volume of sample being collected.

In the emptying position, as shown in FIG. 2, the sample extracting portion 28 is located towards an outer end of the sample housing portion 26. The sample housing portion 26 includes at least one aperture (not shown) which fluidly connects with the annular space 38 when the sample extracting portion 28 is in the emptying position. This permits the sample contained in the annular space 38 to be removed by suitable means, such as the action of gravity.

In the neutral position, the sample extracting portion 28 is located adjacent the inner end of the sample housing portion 26, such that it is adjacent the pipe without being in the pipe flow path.

The supply of air into the first cylinder 40 causes the first piston 32 to move between inner and outer ends of the first cylinder 40, thus causing the sample extracting portion to move between the collecting and emptying positions.

The supply of air into the outer end of the second cylinder 42 causes the second piston 44 to move to the inner end of the second cylinder 42, thus causing the first piston 32 to move partially along the first cylinder 40 and the sample extracting portion to move from the emptying position to the neutral position.

In use, it is envisaged that the sample extracting portion 28 will normally be maintained in the neutral position. Supply of air into the outer end of the first cylinder 40 will cause it to move into the collecting position for a predetermined period of time. Supply of air into the inner ends of both first and second cylinders will then move the sample extracting portion 28 into the emptying position for a predetermined period of time. Finally supply of air into the outer end of the second cylinder 42 will cause the sample extracting portion to return to the neutral position.

When maintenance is required on the sampling device, it will be necessary to move the sample housing portion 26 into the inactive position. This is achieved by turning of the handle 54, which moves the rod 50, the first and second cylinders 40, 42 and the sample housing portion 26 along the side rails 18 in an axial direction towards the second end 14. This movement is effected until the sample housing portion 26 is clear of the knife gate valve 22. The knife gate valve 22 is then moved into the closed configuration, sealing the pipe against the sample housing portion 26. The sample housing portion 26 may then be extracted for maintenance.

Modifications and variations as would be apparent to a skilled addressee are deemed to be within the scope of the present invention. For instance, it will be appreciated that the present invention can be performed with only one cylinder, and not using the neutral position.

The invention claimed is:

1. A sampling device for extracting a sample from a pipe, the sampling device arranged to connect to the pipe comprising:
    a sample housing portion, the sample housing portion being operatively associated with a primary valve, such that the sample housing portion may be fluidly connected to the pipe when the primary valve is in an open configuration, and the primary valve provides a seal between the pipe and the sample housing portion when the primary valve is in a closed configuration; and
    a sample extracting portion, said sample extracting portion being moveable relative to the sample housing portion,
    wherein the sample housing portion is movable relative to the pipe while the sampling device is connected to the pipe, and the primary valve is in the open configuration,
    the sample extracting portion being operatively associated with a first cylinder, the first cylinder being arranged to move with the sample housing portion
    wherein the sample extracting portion includes a spool moveable between a collecting position and an emptying position, the movement of the sample extracting portion being controlled by a first piston within the first cylinder.

2. The sampling device as claimed in claim 1, wherein the first cylinder is coupled to a second cylinder having a second piston, whereby movement of the second piston towards the sample housing portion causes movement of the spool from the emptying position to a neutral position adjacent an inner end of the sample housing portion.

3. The sampling device as claimed in claim 1, wherein the sampling device includes a set of side rails rigidly mounted to the primary valve, and wherein the first cylinder is arranged to move axially along the side rails.

4. The sampling device as claimed in claim 3, wherein the sampling device includes an end plate coupled to the side rails, the end plate having a threaded aperture therein, and whereby the rotation of a threaded rod through the threaded aperture causes movement of the sample housing portion.

5. The sampling device as claimed in claim 1, wherein the primary valve is a knife gate valve.

6. The sampling device as claimed in claim 1, wherein the primary valve is a double knife gate valve.

7. A sampling device for extracting a sample from a pipe, the sampling device arranged to connect to the pipe comprising:
   a sample housing portion, and
   a sample extracting portion, said sample extracting portion being moveable relative to the sample housing portion,
   the sample housing portion being operatively associated with a primary valve, whereby the sample housing portion may be fluidly connected to the pipe when the primary valve is in an open configuration, and the primary valve provides a seal between the pipe and the sample housing portion when the primary valve is in a closed configuration,
   wherein while the sampling device is connected to the pipe, and the primary valve is in the open configuration, the sample extracting portion is moveable inside and outside relative to the pipe, and the sample housing portion is moveable inside and outside relative to the primary valve.

8. The sampling device as claimed in claim 7, wherein the sample extracting portion is operatively associated with a first cylinder, the first cylinder being arranged to move with the sample housing portion.

9. The sampling device as claimed in claim 8, wherein the sample extracting portion includes a spool moveable between a collecting position and an emptying position, the movement of the sample extracting portion being controlled by a first piston within the first cylinder.

10. The sampling device as claimed in claim 9, wherein in the collecting position the spool is outside the sample housing portion, and whereby the spool passes within the sample housing portion when moving between the collecting position and the emptying position.

11. The sampling device as claimed in claim 10, wherein the spool seals against an internal bore of the sample housing portion when passing within the sample housing portion.

12. The sampling device as claimed in claim 9, wherein the sample housing portion has an aperture which permits passage of a sample from the spool through the sample housing portion for collection when the spool is in the emptying position.

13. The sampling device as claimed in claim 9, wherein the first cylinder is coupled to a second cylinder having a second piston, whereby movement of the second piston towards the sample housing portion causes movement of the spool from the emptying position to a neutral position adjacent an inner end of the sample housing portion.

14. The sampling device as claimed in claim 8, wherein the sampling device includes a set of side rails rigidly mounted to the primary valve, and wherein the first cylinder is arranged to move axially along the side rails.

15. The sampling device as claimed in claim 14, wherein the sampling device includes an end plate coupled to the side rails, the end plate having a threaded aperture therein, and whereby the rotation of a threaded rod through the threaded aperture causes movement of the sample housing portion.

16. The sampling device as claimed in claim 7, wherein the primary valve is a knife gate valve.

17. The sampling device as claimed in claim 7, wherein the primary valve is a double knife gate valve.

18. The sampling device as claimed in claim 7, wherein the sample extracting portion includes a spool moveable, when the primary valve is in the open configuration, between a collecting position outside the sample housing portion and a neutral position within an internal bore of the sample housing portion, the spool sealing against the internal bore of the sample housing position when in the neutral position.

19. The sampling device as claimed in claim 7, wherein the primary valve has a central bore when in the open configuration, and the sample housing portion seals against the central bore when extending through the primary valve.

* * * * *